United States Patent [19]

Skiba et al.

[11] Patent Number: 6,047,706
[45] Date of Patent: Apr. 11, 2000

[54] HEAD BATHING ARRANGEMENT

[75] Inventors: Barbara T. Skiba, Chicago; Keith M. Simon, Crystal Lake, both of Ill.

[73] Assignee: Sage Products, Inc., Crystal Lake, Ill.

[21] Appl. No.: 09/257,224

[22] Filed: Feb. 25, 1999

[51] Int. Cl.⁷ ................................................. A45D 19/18
[52] U.S. Cl. ............................. 132/200; 132/212; 2/174
[58] Field of Search ................................ 132/200, 221, 132/270, 272, 319, 212; 2/174, 171.2, 209.14

[56] References Cited

U.S. PATENT DOCUMENTS

| | | | |
|---|---|---|---|
| 2,424,129 | 7/1947 | Vincelle | 2/174 |
| 2,507,386 | 5/1950 | Spiegel | 132/212 |
| 2,781,764 | 2/1957 | Miller | 132/212 |
| 2,858,834 | 11/1958 | Givens | 132/212 |
| 3,088,469 | 5/1963 | Berryhill et al. | 132/212 |
| 3,261,027 | 7/1966 | Lambert | 2/174 |
| 3,954,113 | 5/1976 | Bohrer et al. | 132/200 |
| 4,296,763 | 10/1981 | Priest et al. | 132/200 |
| 5,265,278 | 11/1993 | Watanabe | 2/174 |

*Primary Examiner*—Todd E. Manahan
*Attorney, Agent, or Firm*—Lee, Mann, Smith, McWilliams, Sweeney & Ohlson

[57] ABSTRACT

A head bathing system for haircare. The system is composed of an outer cap having a head-receiving aperture, an inner, absorbent liquid-holding layer, and a flexible gathering for the cap at the aperture. The liquid-holding layer is impregnated with a cleansing solution. To clean a person's hair, the system is applied to the person's head, which is massaged through the cap to cause the cleansing solution to wet the person's hair. After sufficient cleaning, the system is removed from the person's head. Because of the nature of the liquid-holding layer, it reabsorbs much of the cleansing solution before the system is removed from the person's head.

17 Claims, 2 Drawing Sheets

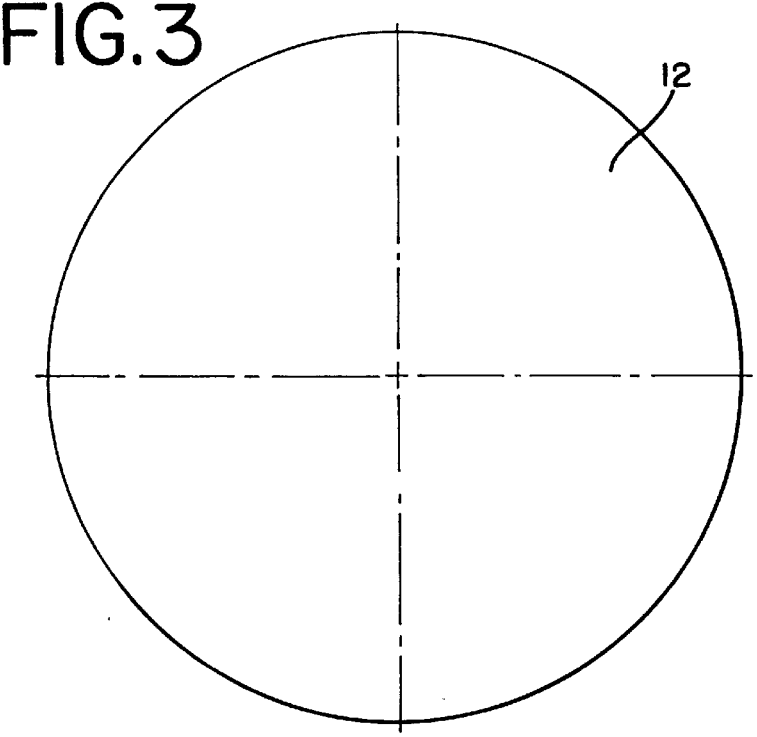
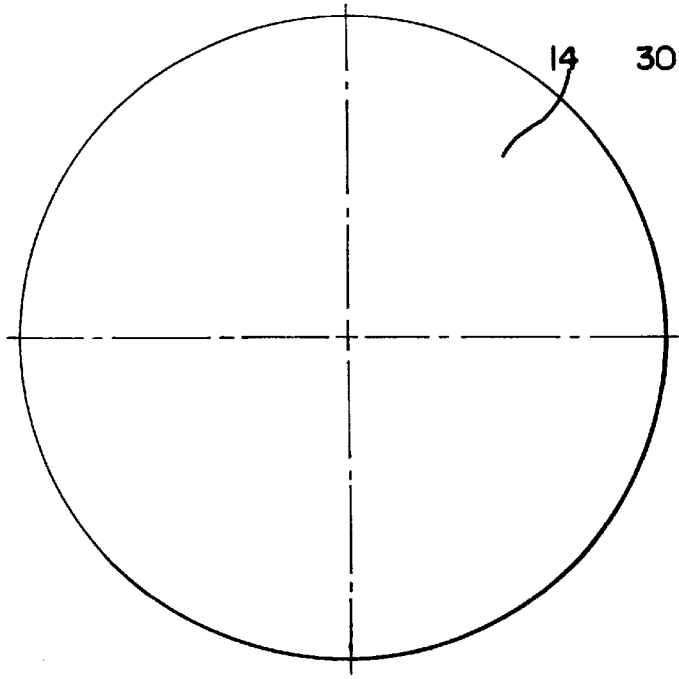
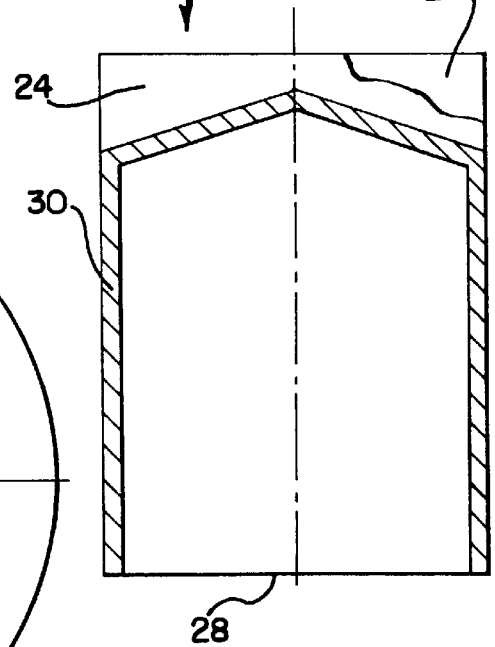

HEAD BATHING ARRANGEMENT

BACKGROUND OF THE INVENTION

This invention relates to personal hygiene, and in particular to a head bathing system and method of bathing a person's head, where the system is self-contained and disposable.

Personal hygiene of a patient or a person who does not have readily available bathing facilities is always a problem. Many different devices and systems have been developed for these purposes. For example, U.S. Pat. No. 5,725,311, assigned to the assignee of the present application, discloses a bathing system employing a series of washcloths disposed in a resealable package. The washcloths, which are impregnated with a cleansing solution, can be withdrawn and used for body cleansing, and then discarded.

While washcloths function well for cleansing most body areas, the hair provides a particular challenge simply because hair, rather than a body surface, must be cleaned. Various devices have been developed in the past for such purposes. For example, U.S. Pat. No. 5,099,865 discloses a hair washing aid comprising an outer hood which is fitted around the person's head. Water and shampoo are added externally through an inlet, the hair is washed, and run off is captured in an extension. In the ideal scenario, the hair washing aid is able to capture all excess moisture, but in reality, water and shampoo are inevitably spilled.

U.S. Pat. No. 2,424,124 discloses a shampoo cap which also fits around the head and has a series of spaced suction cups which are used for massaging the head and hair after shampoo has been applied. However, no means is provided for rinsing the shampoo, which must be removed, presumably by removing the shower cap.

An automatic, but highly complex, hair-washing machine is disclosed in U.S. Pat. No. 4,769,861. It is not self contained, is not disposable, and given its complexity, is not feasible.

Hair-coverings or caps are disclosed in U.S. Pat. Nos. 3,138,801; 3,327,720 and 3,399,621, These are simply hair protection or covering devices, and are not used for hair cleansing.

SUMMARY OF THE INVENTION

The invention is directed to a method of bathing a person's hair. That method comprises the steps of providing a substantially fluid-impervious cap with a head-receiving aperture, providing a liquid-holding layer capable of being generally coextensive with the cap, applying a cleansing solution to at least one of the person's hair and the liquid-holding layer, and then applying the cap and the layer to the person's head. The person's head is then massaged through the cap and the liquid-holding layer to cause the cleansing solution to permeate the person's hair. Finally, the cap and the layer are then removed once the bathing of the person's hair has been completed.

In accordance with the preferred form of the invention, the liquid-holding layer comprises an absorbent material. The method further includes reabsorbing a portion of the cleansing solution in the absorbent material before the cap is removed.

A head bathing arrangement according to the invention comprises an outer package, means for opening the outer package, and a head bathing system which comprises a substantially fluid-impervious cap within the outer package. The cap has a head-receiving aperture and includes an inner, liquid-holding layer generally coextensive with the cap. The liquid-holding layer is impregnated with a cleansing solution.

In accordance with the preferred form of the invention, the outer package comprises opposite halves which are joined by a peelable seal. The opening means comprises a flap extending from at least one of the halves, and preferably opposite flaps, one extending from each of the halves.

The cap comprises a plastic film, which is formed in a generally circular sheet. The liquid-holding layer comprises an absorbent fabric, which is preferably non-woven. The fabric is formed to release liquid when compressed, and then reabsorb released liquid before the head-bathing system is removed from a person's head.

In accordance with the preferred form of the invention, the gathering comprises an elastic band. Also, the liquid-holding layer is preferably affixed to the cap, with the liquid-holding layer and the flexible gathering being affixed adjacent the head-receiving aperture.

BRIEF DESCRIPTION OF THE DRAWINGS

The invention is described in greater detail in the following description of an example embodying the best mode of the invention, taken in conjunction with the drawing figures, in which:

FIG. 3 is a plan view of the fluid-impervious cap according to the invention, before formation, FIG. 4 is a plan view of the liquid-holding layer according to the invention, and FIG. 5 is a cross-sectional view of one form of outer package for packaging the head bathing system according to the invention, with a portion cut away to show detail.

DESCRIPTION OF EXAMPLES EMBODYING THE BEST MODE OF THE INVENTION

Figure 1:
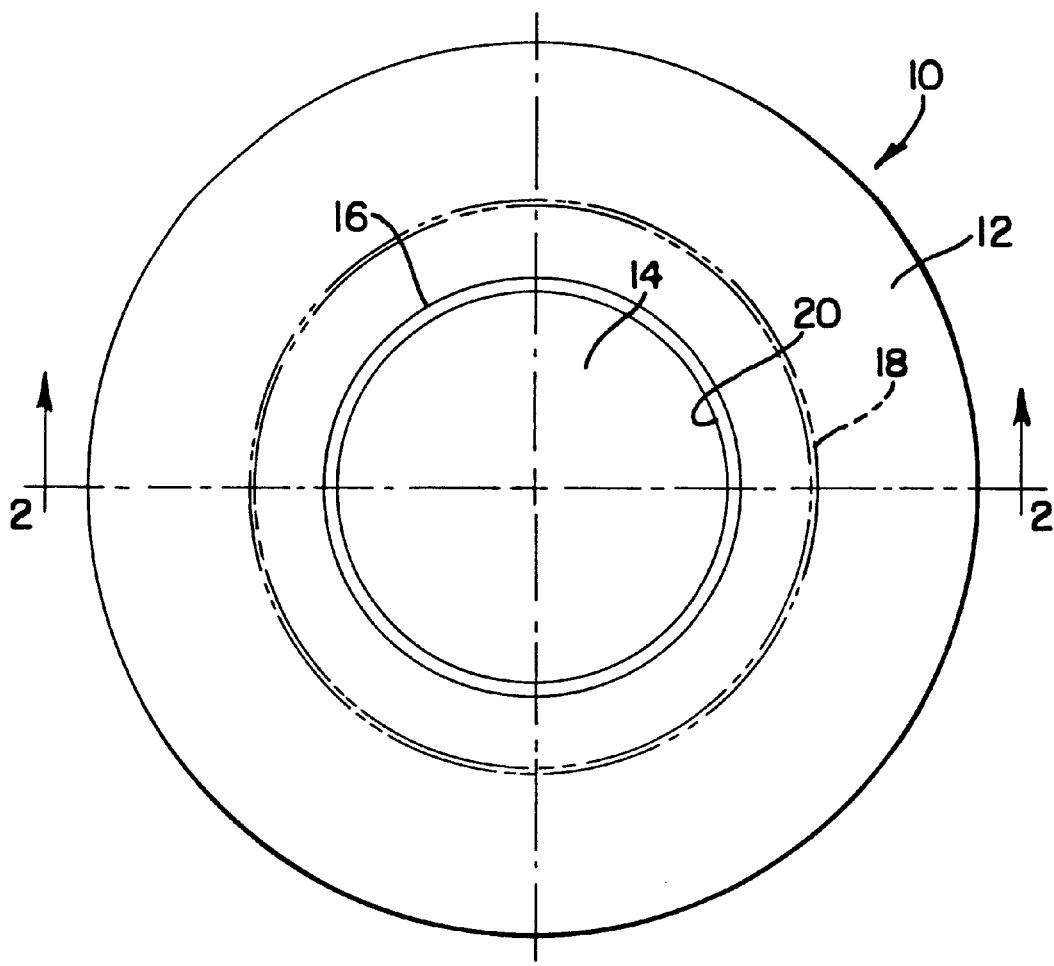
FIG. 1 is a plan view of a head bathing system according to the invention.

A head bathing system according to the invention is designated generally at 10 in the drawing figures. It comprises an outer, pliant, substantially fluid impervious cap 12, an inner, absorbent liquid-holding layer 14, and a flexible gathering 16.

The cap 12 preferably comprises a plastic film, such as vinyl or polyethylene, which is flexible, soft, quiet and comfortable, yet substantially fluid impervious. Preferably the plastic film is formed generally from a circular sheet as shown in FIG. 3, although other shapes will be apparent, and therefore the circular sheet is only preferred. The sheet could be square, oblong or any other shape so long as it can be gathered about the head in the manner described herein.

The liquid-holding layer 14 is preferably formed from a fabric. The fabric can be woven or non-woven, although non-woven is preferred, and the non-woven fabric can be made from any means of mechanically intermingling the fibers of the fabric, such as from needle punching or water jet commingling. Preferably the liquid-holding layer 14 is generally co-extensive with the cap 12, and is secured thereto. As illustrated in FIG. 1, the liquid-holding layer can be secured to the cap 12 at 18 by any well-known method, such as sewing, heat staking, or ultrasonic welding. Also, although the point of securing the layer 14 to the cap 12 is shown spaced substantially from the gathering 16, the gathering 16 and the securing 18 can be much closer to one another, or even coextensive. Typically, the layer 14 is somewhat smaller in diameter, as the relative sizes in FIGS. 3 and 4 illustrate.

The gathering 16 preferably comprises an elastic band. The elastic band is affixed to the cap 12 at the outer periphery thereof, forming an expandible head-receiving aperture 20. The flexible gathering 16 can be any conventional type of elastic band, and can be installed in the cap 12 in a conventional fashion which forms no part of the invention.

Preferably, the liquid-holding layer 14 is impregnated with a cleansing solution. The cleansing solution contains, at minimum, water and a cleaning agent. Preferably, it also includes a conditioner, an antimicrobial agent, a preservative, an antifoaming agent and a fragrance.

While many different and equivalent constituents can be used for the cleansing solution, preferably the cleaning agent comprises disodium cocoamphodiacetate. Preferably the conditioner comprises isostearomidapropyl morpholine lactate. The antimicrobial agent preferably comprises DMDM hydondoin. The preservative preferably comprises phenonip and the antifoaming agent comprises a simethicone emulsion. Finally, if a fragrance is employed, a preferred fragrance is sensitech neutrex.

Figure 2:
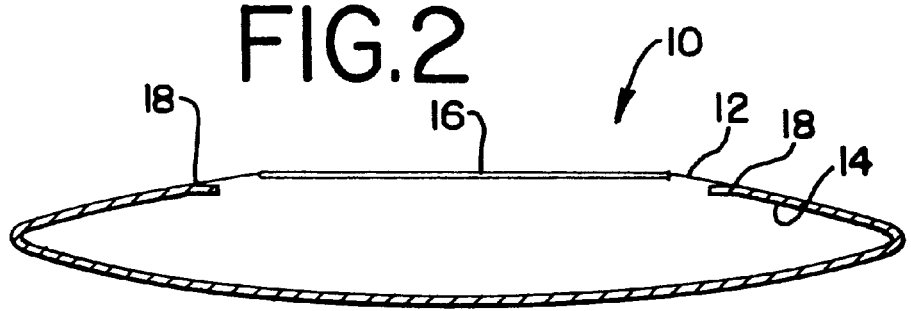
FIG. 2 is a cross-sectional view of the head bathing system according to the invention, taken along lines 2—2 of FIG. 1.

The head bathing system 10 can be manufactured in any of a number of well-known fashions. For example, after the cap 12 and liquid-holding layer 14 are cut to their respective shapes shown in FIGS. 3 and 4, the liquid-holding layer 14 can be laid on the cap 12 and stitch at 18, while both are still flat. Then, the elastic band for the flexible gathering 16 can be stretched and installed at the outer periphery of the still-flat cap 12. When the elastic band is then released, the head bathing system assumes the configuration shown in FIGS. 1 and 2, with obvious blousing (not illustrated) as the elastic band of the flexible gathering 16 contracts to form the small aperture 20 shown in FIG. 1. The cleansing solution can then be poured, sprayed or otherwise introduced to the liquid-holding layer 14 to complete the head bathing system 10.

In use, the head bathing system 10 is fitted around a person's head like a conventional shower cap, with the flexible gathering 16 holding the head bathing system 10 snugly about the person's head. The person's head is then massaged through the cap 12 and the liquid-holding layer 14, causing the cleansing solution to permeate the person's hair. Since the liquid-holding layer 14 is capable of reabsorbing excess liquid, when the bathing step has been completed, excess liquid is reabsorbed in the layer 14, and the head bathing system is then removed. Any liquid remaining in the person's hair can be allowed to evaporate, or can be further dried, as desired.

Preferably, the head bathing system 10 is provided as a complete unit; that is, fully assembled and with the cleansing solution permeating the liquid-holding layer 14. Alternatively, the head bathing system 10 can be provided without the liquid-holding layer being saturated with the cleansing solution, or even without the liquid-holding layer being affixed to the cap 12.

When the head bathing system 10 is provided in the preferred form, it must be sealed in an outer package in order to prevent evaporation of the cleansing solution. One form of outer package 22 is shown in FIG. 5. The outer package 22 comprises a pair of opposite halves 24 and 26, which are preferably plastic sheets. They are one atop the other, and preferably coextensive, with the sheet 24 being shown atop the sheet 26 in FIG. 5. The sheets may be separate, or can extend from a common fold or end seal 28. The head bathing system 10, when completed, is folded and then installed between the sheets 24 and 26. The sheets 24 and 26 are then joined by a peelable seal 30. As shown in FIG. 5, the seal 30 continues along the opposite side edges of the package 22, but terminates short of one end of the package 22. This results in opposite flaps which can be easily grasped by a user and peeled apart to remove the head-bathing system 10 (not illustrated in FIG. 5) for use.

The sheets 24 and 26 of the outer package 22 are preferably formed from plastic, which is readily transparent to microwave energy. For comfort during use, the package 22, containing the head bathing system 10, can be heated in a microwave oven before use.

The invention has many advantages and features. Because the head bathing system 10 is preferably contained within the outer package 22 before use, an acceptable and desired amount of cleansing solution is readily available directly at the point of use of the head bathing system 10. Also, because the outer package 22 is composed of opposite peelable sheets 24 and 26, the package 22 is easy to open. Furthermore, the package 22 can be employed as a tote during both microwave heating and transportation to the point of use of the head bathing system 10.

The plastic film of the cap 12, which preferably is vinyl, is flexible, soft, quiet and comfortable. The flexible gathering 16, when the head bathing system is on a person's head, serves to contain the cleansing solution within the cap 12 and to gently secure the cap 12 to the person's head during bathing.

Since the liquid-holding layer 14 is preferably a fabric, it holds the cleansing solution uniformly throughout its fibers, and then, during use, readily relinquishes the cleansing solution to the person's hair for head bathing. When the bathing process is completed, however, the fabric then is capable of reabsorbing the solution to leave the hair relatively dry when the head bathing system 10 is removed from the person's head.

Preferably, the head bathing system 10 is designed for single use, but can also be reused.

Various changes can be made to the invention without departing from the spirit thereof or scope of the following claims.

What is claimed is:

1. A method of bathing a person's hair, comprising the steps of
   a. providing a substantially fluid-impervious, flexible cap with a head-receiving aperture,
   b. providing a liquid-holding layer capable of being generally coextensive with the cap, but with the liquid-holding layer being smaller in dimension than the cap,
   c. securing the liquid-holding layer to the cap only along an outer periphery of the liquid-holding layer,
   d. applying a cleansing solution to at least one of the person's hair and the liquid-holding layer,
   e. applying the cap and layer to the person's head,
   f. massaging the person's head through the cap and the layer to cause the cleansing solution to permeate the person's hair, and
   g. removing the cap and the layer.

2. The method according to claim 1 in which the liquid-holding layer comprises an absorbent material, and the method further includes reabsorbing a portion of the cleansing solution in the absorbent material before method step f.

3. A method of bathing a person's hair, comprising the steps of
   a. providing a head bathing system comprising a substantially fluid-impervious, flexible cap, an inner liquid-holding layer generally coextensive with the cap, said liquid-holding layer being smaller in dimension than the cap, and a cleansing solution impregnating the liquid-holding layer,
   b. securing the liquid-holding layer to the cap only along an outer periphery of the liquid-holding layer,
   c. applying the head bathing system to a person's head,
   d. massaging the person's head through the cap and the layer to cause the cleansing solution to permeate the person's hair, and
   e. removing the heading bathing system from the person's head.

4. The method according to claim 3 in which the liquid-holding layer comprises an absorbent material, and the method further includes reabsorbing a portion of the cleansing solution in the absorbent material before method step d.

5. The method according to claim 3 including heating the cleansing solution of the head bathing system prior to step "a".

6. A head bathing arrangement, comprising
   a. an outer package,
   b. means for opening the outer package, and
   c. a head bathing system comprising a substantially fluid-impervious, flexible cap within the outer package, said cap having a head-receiving aperture and including an inner, liquid-holding layer generally coextensive with said cap but smaller in dimension than the cap, said layer being impregnated with a cleansing solution, and further having a flexible gathering for said cap proximate said aperture.

7. A head bathing arrangement according to claim 6 in which said outer package comprises opposite halves joined by a peelable seal, and said opening means comprises a flap extending from at least one of said halves.

8. A head bathing arrangement according to claim 7 including a flap extending from each of said halves.

9. A head bathing arrangement according to claim 6 in which said cap comprises a plastic film.

10. A head bathing arrangement according to claim 9 in which said film comprises a generally circular sheet.

11. A head bathing arrangement according to claim 6 in which said liquid-holding layer comprises an absorbent fabric.

12. A head bathing arrangement according to claim 11 in which said fabric is non-woven.

13. A head bathing arrangement according to claim 11 in which said fabric releases liquid when compressed and is capable of reabsorbing released liquid.

14. A head bathing arrangement according to claim 6 in which said gathering comprises an elastic band.

15. A head bathing arrangement according to claim 6 in which said liquid-holding layer is affixed to said cap.

16. A head bathing arrangement according to claim 15 in which said layer and said flexible gathering are affixed to said cap adjacent said aperture.

17. A head bathing arrangement according to claim 6 in which said cleansing solution includes water and a cleaning agent.

* * * * *